United States Patent [19]

Seifried

[11] 4,341,735
[45] Jul. 27, 1982

[54] SAMPLE CARRIER MATERIAL HANDLING APPARATUS

[75] Inventor: Paul E. Seifried, New City, N.Y.

[73] Assignee: American Cyanamid Company, Stamford, Conn.

[21] Appl. No.: 134,843

[22] Filed: Mar. 28, 1980

[51] Int. Cl.³ .................. G01N 1/04; G01N 1/10; G01N 33/48
[52] U.S. Cl. .................. 422/66; 73/864.44; 83/167; 422/99; 435/292
[58] Field of Search .............. 422/99, 100, 104, 66; 73/864.44; 83/167; 435/292, 287

[56] References Cited

U.S. PATENT DOCUMENTS

| | | |
|---|---|---|
| 3,120,778 | 2/1964 | Brye ............................ 83/167 |
| 3,547,781 | 12/1970 | Guigan et al. ................ 422/100 |
| 3,999,949 | 12/1976 | Andersson et al. ........... 422/100 |
| 4,281,546 | 8/1981 | Fraleigh ..................... 73/864.44 |

*Primary Examiner*—Ronald E. Serwin
*Attorney, Agent, or Firm*—Charles F. Costello, Jr.

[57] ABSTRACT

An apparatus for handling sample carrier material is described. The apparatus comprises (a) a punch holder; (b) at least one punch means raisably and lowerably mounted on the holder; (c) a die having an upper and a lower surface, the thickness of the die being less than the punch means lower travel from the die upper surface, the die in functional alignment with the punch means, and the die upper and lower surface in a cutting and delivery position, respectively, of the sample material; and (d) control means to regulate the punch means.

1 Claim, 5 Drawing Figures

SAMPLE CARRIER MATERIAL HANDLING APPARATUS

FIELD OF THE INVENTION

This invention concerns a novel sample carrier material handling apparatus. This apparatus is capable of cutting, positioning and depositing sample carrier material, such as blotter paper, porous polymers and the like. This apparatus is useful for cutting, positioning and depositing such sample carrier material onto materials such as agar or gelatinous media of biological assays. Such an assay is agar-diffusion assay for screening biological or anti-microbial agents.

BACKGROUND OF THE INVENTION

This invention is concerned with a novel device that has been designed to combine and facilitate several time consuming functions normally required in a screening process of biological or anti-microbial agents. Typically such screening requires that an agar plate be prepared with an inoculum of a particular organism. Upon such innoculated agar plate is positioned a number of discs of sample carrier material impregnated, or to be impregnated, with a particular biological agent. This agent may be, for example, a sample of particular bacteria or a chemical agent. After incubating the agar plate with the impregnated sample carrier materials the pattern of growth upon the plate is used to identify the particular action of the test material.

To provide sample carrier material segments on agar plates presently requires that the desired location of the sample carrier material segments be marked manually. The individual sample carrier material segments such as blotter paper discs must then be rapidly manually placed on the plate in a precise manner. The several operations of this procedure require a considerable amount of time to perform and increase the incidence of accidental infection and inaccurate test results.

SUMMARY OF THE INVENTION

This invention is concerned with a novel sample carrier material handling apparatus for cutting, positioning and depositing from one to a plurality of sample carrier material segments onto a gelatinous media plate an agar plate or other similar article. The plates thus prepared are utilized in a number of biological procedures, testing the biological activity of the test material which is adsorbed onto the sample carrier material. Such test material may be adsorbed onto sample carrier material either before or after placement on the agar plate. In one embodiment the sample cutting material is positioned in the apparatus of the present invention in sheet form. Then by a punching means segments are punched out of the sheet. These sample carrier material segments then drop onto an agar plate positioned below the punching means. This invention will be better understood by reference to the figures.

DETAILED DESCRIPTION OF THE INVENTION

This apparatus is capable of cutting, positioning and depositing sample carrier material such as blotter paper, porous polymers and the like. Many embodiments of this invention will be immediately obvious to those skilled in the art without departing from the spirit of the invention. The following description is intended to be merely illustrative of the invention and in no way limiting. This invention will be limited only by the claims.

Figure 1:
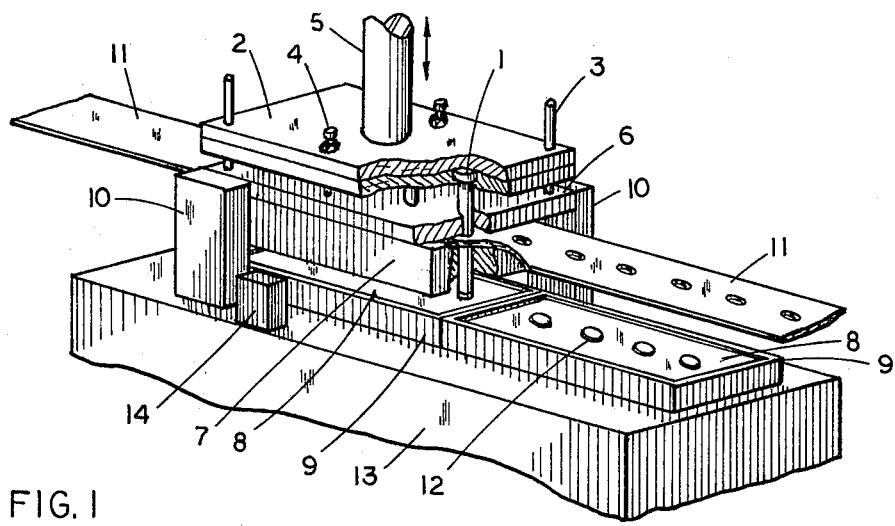
FIG. 1 is a side perspective view with partial cutaway of the sample carrier material handling apparatus.

FIG. 1 is a side perspective view of the sample carrier material handling apparatus with partial cutaway. A punch member (1) vertically mounted is seen to be held by punch holder means (2) capable of holding from 1 to a plurality of punch members. Said punch holder means is vertically raisably and lowerably mounted on guide bars (3). The maximum excursion of said punch holder means being limited by stop means (4). A cutting stroke actuator linking means (5) is shown capable of compressing said punch means in a cutting stroke such cutting stroke actuator linking means being motively connected to a drive means, (not shown), such as a hydraulic or pneumatic press or the like.

A guide means (6), here in the form of a plate, which bears from one to a plurality of holes maintains punch means, which pass through the said guide means, in alignment with die (7) having an upper surface and a lower surface. Sample carrier material discs (12) punched out of sample carrier material sheets (11) is deposited on gel (8) of gel plates (9) when in proper position. Die support members (10) maintains said die in proprer position over said gel plate, said support member being borne on machine table (13). The sequential operation of the above steps is integrated by control means (14). This control means will be understood to be comprised of timing mechanisms such as timing chains, clock mechanisms, computer programs and the like and combinations thereof and without limitation, alone and in combination with sensor mechanisms such as electric eyes, magnetic contact switches, and pressure contact switches and the like alone or in combination, and without limitation.

FIGS. 2, 3, 4, and 5 are cutaway sequential views of a sample carrier material cutting and placement stroke.

Figures 2, 3, 4, 5:
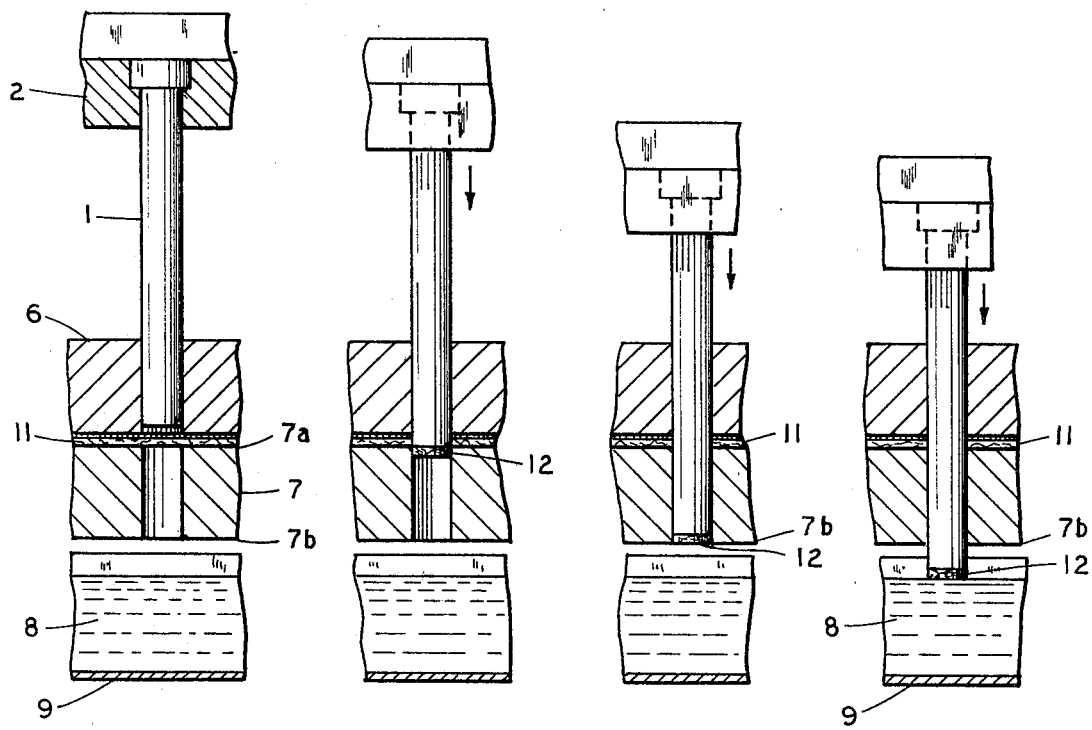
FIGS. 2, 3, 4 and 5 are cutaway sequential views of a sample carrier material cutting and placement stroke.

In these views (beginning with FIG. 2) a punch (1) held in punch holder (2) travels through guide plate (6) to cut sample carrier material (11) [FIG. 3] at the upper surface of die (7a) forcing the newly cut disc (12) down the thickness of said die to the lower surface of the die (7b) [FIG. 4] onto gel (8) contained in gel carrier (9) [FIG. 5], said lower surface of die (7b) is the delivery position of disc (12) suitable for dropping the disc onto a predeterminable spot on the gel, as regulated by the control means. I claim:

1. An apparatus for handling sample carrier material comprising:
   (a) a punch holder;
   (b) at least one punch means raisably and lowerably mounted on said holder;
   (c) a die having an upper and a lower surface, the thickness of said die being less than the punch means lower travel from said die upper surface, said die in functional alignment with said punch means, and said die upper and lower surface in a cutting and delivery position, respectively, of said sample material; and
   (d) control means to regulate said punch means whereby sample carrier material is placed on said die upper surface; said punch means is lowered by said control means such that said sample material is cut and forced through said die by said punch means, is delivered out of said die at said lower surface and is deposited onto a media; and said punch means is raised by said control means.

* * * * *